(12) United States Patent
Bloch et al.

(10) Patent No.: US 10,342,648 B2
(45) Date of Patent: *Jul. 9, 2019

(54) POWERED TOOTHBRUSH

(71) Applicant: Colgate-Palmolive Company, New York, NY (US)

(72) Inventors: Brian Bloch, Hillsborough, NJ (US); Lars Ralf Rainer Lieberwirth, Glashuetten (DE)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,490

(22) PCT Filed: Dec. 17, 2014

(86) PCT No.: PCT/US2014/070939
§ 371 (c)(1),
(2) Date: Jun. 20, 2016

(87) PCT Pub. No.: WO2015/095384
PCT Pub. Date: Jun. 25, 2015

(65) Prior Publication Data
US 2016/0338807 A1    Nov. 24, 2016

(30) Foreign Application Priority Data

Dec. 19, 2013  (CN) .......................... 2013 1 0702170

(51) Int. Cl.
*A46B 15/00*    (2006.01)
*A61C 17/22*    (2006.01)
(Continued)

(52) U.S. Cl.
CPC .......... *A61C 17/221* (2013.01); *A46B 5/0095* (2013.01); *A46B 9/04* (2013.01);
(Continued)

(58) Field of Classification Search
CPC . A46B 15/0006; A61C 17/221; A61C 17/225; G06F 3/044
See application file for complete search history.

(56) References Cited

U.S. PATENT DOCUMENTS

| 2002/0174498 A1 | 11/2002 | Li |
| 2013/0093500 A1 | 4/2013 | Bruwer |

(Continued)

FOREIGN PATENT DOCUMENTS

| CN | 2010-44776 | 4/2008 |
| EP | 2573513 | 3/2013 |

(Continued)

OTHER PUBLICATIONS

Corresponding International Search Report and Written Opinion for PCT/US2014/070939 dated Mar. 6, 2015.

*Primary Examiner* — Randall E Chin

(57) ABSTRACT

A powered toothbrush apparatus with capacitive touch control is disclosed. The tooth brush includes a head portion having an oscillating tuft block driven by a motor, a handle portion, and an elastically deformable capacitive touch control panel mounted in the handle portion. In one embodiment, the control panel includes a plurality of capacitance sensor buttons each having movable sensor targets paired with a corresponding capacitance sensor electrically connected to a programmable microprocessor. Applying finger pressure on the control panel adjacent a sensor target changes capacitance of the sensor button. The microprocessor detects the change in capacitance, which controls the operating mode of the toothbrush including on/off, motor speed, brushing mode such as pulse, or other. A related operating method is disclosed.

8 Claims, 13 Drawing Sheets

(51) Int. Cl.
*G06F 3/044* (2006.01)
*A46B 5/00* (2006.01)
*A46B 9/04* (2006.01)
*A61C 17/34* (2006.01)
*B08B 1/00* (2006.01)
*H03K 17/96* (2006.01)

(52) U.S. Cl.
CPC ...... *A46B 15/0006* (2013.01); *A46B 15/0008* (2013.01); *A61C 17/225* (2013.01); *A61C 17/3445* (2013.01); *B08B 1/002* (2013.01); *G06F 3/044* (2013.01); *H03K 17/962* (2013.01); *A61C 17/34* (2013.01)

(56) References Cited

U.S. PATENT DOCUMENTS

| | | | |
|---|---|---|---|
| 2013/0177863 A1 | 7/2013 | Shreve | |
| 2014/0123414 A1* | 5/2014 | Okazaki | A61C 17/221 |
| | | | 15/22.1 |
| 2014/0250612 A1* | 9/2014 | Curry | A61C 17/221 |
| | | | 15/22.1 |

FOREIGN PATENT DOCUMENTS

| | | |
|---|---|---|
| WO | 2012/042493 | 4/2012 |
| WO | WO2013021716 | 2/2013 |

* cited by examiner

POWERED TOOTHBRUSH

CROSS-REFERENCE TO RELATED PATENT APPLICATIONS

The present application is a U.S. national stage application under 35 U.S.C. § 371 of PCT Application No. PCT/US2014/070939, filed Dec. 17, 2014, which claims priority to Chinese Patent Application No. 201310702170.X, filed on Dec. 19, 2013, the entireties of which are incorporated herein by reference.

BACKGROUND

Powered toothbrushes are known having various movable tuft blocks on which tooth cleaning elements are mounted. The movable tuft blocks are driven by an electric motor configured to oscillate the tuft block in a predetermined brushing motion. Various types of approaches including mechanical or electronic switches may be used to control motor speed or other functions of the tooth brush. Improvements in such powered toothbrush controls are desirable.

BRIEF SUMMARY

According to one embodiment, a powered toothbrush apparatus with capacitive touch control includes a motor, a handle portion, a capacitive touch control panel in the handle portion, and a plurality of capacitance sensors operably associated with the control panel. Each of the plurality of capacitance sensors has a capacitance value that is changed by a user pressing a specific location of the control panel, thereby activating the capacitance sensor. Further provided is a microprocessor in the handle portion which is electrically connected to the plurality of capacitance sensors and the motor. The microprocessor is configured to: (1) detect changes in the capacitance values of the plurality of capacitance sensors; and (2) change an operating mode of the toothbrush apparatus based on the changes in capacitance values. In one embodiment, the operating mode changed is motor speed. In the same or another embodiment, the operating mode changed is an on or off state of the motor. The toothbrush may further include a head portion including an oscillating tuft block driven by the motor, the tuft block including a plurality of tooth cleaning elements. In one embodiment, the motor may be mounted in the handle portion. In other embodiments, the motor may be mounted in the head portion.

According to another embodiment, a powered toothbrush apparatus with capacitive touch control includes a motor, a handle portion, and a capacitive touch control panel mounted in the handle portion. The control panel is elastically deformable in response to the application of inward directed finger pressure by a user. A plurality of capacitance sensor buttons are mounted in the handle portion, each capacitance sensor button including a capacitance sensor and a corresponding movable conductive sensor target disposed on the control panel above the sensor. The sensor target is movable towards its corresponding sensor in response to a user applying finger pressure to the control panel adjacent the sensor target which changes a capacitance of the sensor button. A microprocessor is mounted in the handle portion and electrically connected to the sensors and the motor. The microprocessor is configured to: detect changes in the capacitance values of the plurality of capacitance sensor buttons; and change speed of the motor based on detecting changes in the capacitance values of the plurality of capacitance sensor buttons. In various embodiments, the user pressing a first capacitance sensor button turns the motor on or off. The motor may further not be turned on or off unless the user presses and holds the first capacitance sensor button for a minimum period of time. The user pressing a second capacitance sensor button changes speed of the motor. Pressing the second capacitance button multiple successive times may cycle the motor between a higher speed and a lower speed. In some embodiments, pressing the second capacitance button further initiates a pulse mode in which the motor alternatingly cycles between two speeds for a period of time at each speed.

A method for controlling a powered toothbrush apparatus is provided. The method includes: providing a powered toothbrush apparatus including a handle portion, a motor, an elastically deformable capacitive touch control panel mounted in the handle portion and including a plurality of capacitance sensor buttons, each capacitance sensor button including a capacitance sensor and a corresponding sensor targets movable by deforming the control panel, each capacitance sensor button having a capacitance that is changed by an inward pressing action on the control panel adjacent the sensor target; a user pressing a first capacitance sensor button; a microprocessor disposed in the handle portion detecting a change in capacitance of the first capacitance sensor button; and the microprocessor turning the motor of toothbrush apparatus on in response to the detected change in capacitance of the first capacitance sensor button. In one embodiment, the method further includes: the user pressing a second capacitance sensor button; and the microprocessor changing speed of the motor in response to the detected change in capacitance of the second capacitance sensor button. The method may further include: the user repeatedly pressing the second capacitance sensor button; and the microprocessor changing speed of the motor in response to the detected change in capacitance of the second capacitance sensor button.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
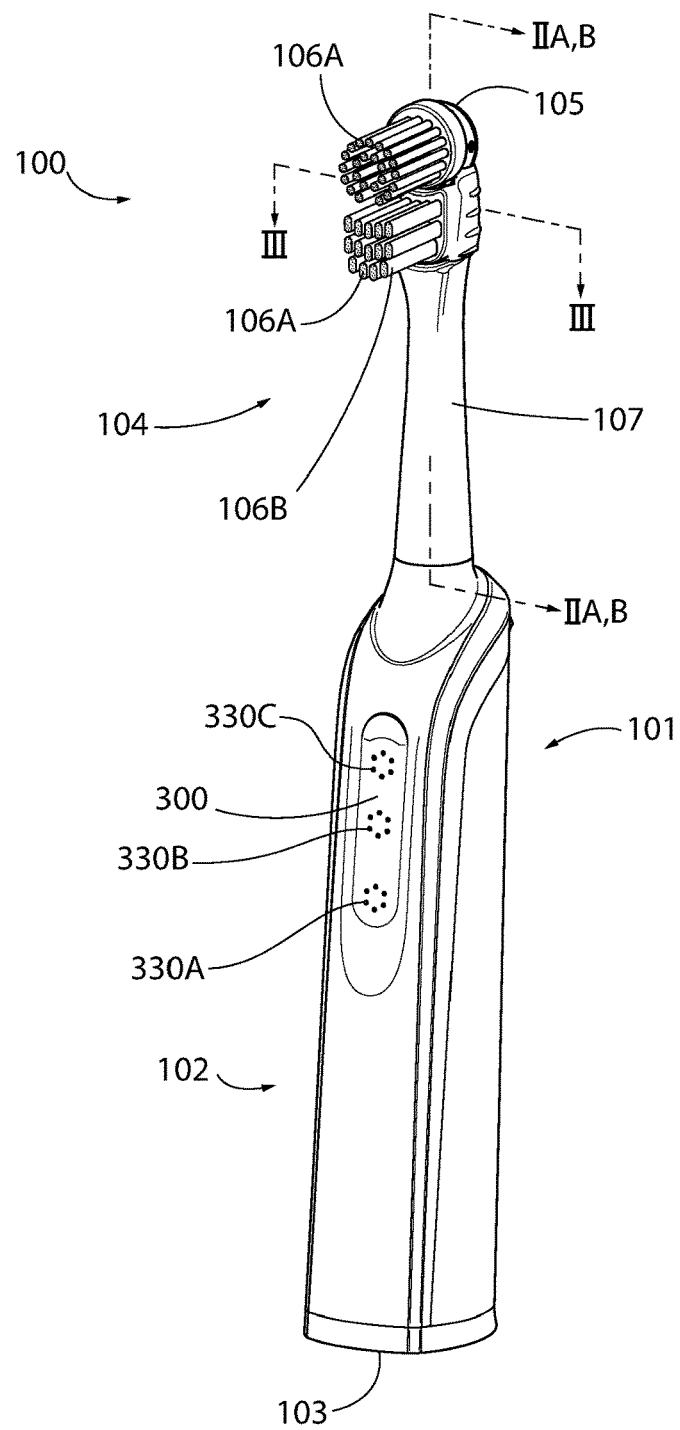
FIG. 1 is a perspective view of a powered toothbrush according to the present disclosure.

All drawings are schematic and not necessarily to scale.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

FIG. 1 depicts a non-limiting exemplary embodiment of an oral care implement in the form of an electric-powered toothbrush 100. Toothbrush 100 includes an elongated body 101 including a handle portion 102 defining a proximal end 103, a head portion 104 defining a distal end 105, and a longitudinal axis LA extending between the proximal and distal ends. Head portion 104 supports a plurality of tooth cleaning elements 106. In one embodiment, head portion 104 may be detachably mounted to handle portion 102 to form a replaceable unit or refill thereby allowing a user to replenish the head portion after the tooth cleaning elements 106 have been worn and/or to change the type of tooth cleaning elements. Accordingly, a separable joint is formed between the head and handle portions 104, 102 of toothbrush 100 in such embodiments.

Handle portion 102 and head portion 104 of toothbrush 100 may be constructed of a material or combination of materials having suitable rigidity for grasping/handling the toothbrush and supporting the tooth cleaning elements 106, respectively. Suitable exemplary materials that may be used include, without limitation, hard plastics, such as polyethylene, polypropylene (PP), polyamide, polyester, cellulosics, SAN, acrylic, ABS and other thermoplastics suitable for toothbrush manufacture. The handle portion 102 and head portion 104 may be made of the same or different materials in various embodiments.

Figure 7:
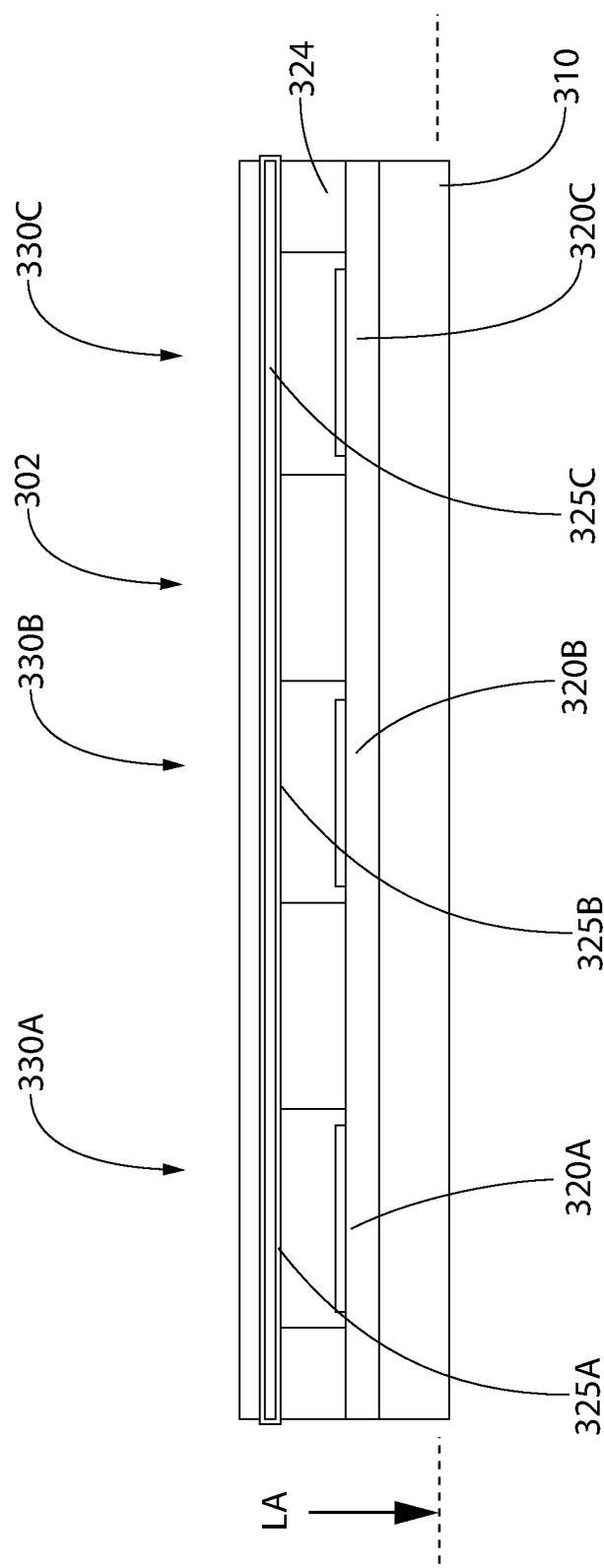
FIG. 7 is a side cross-sectional view of a linear array of the capacitive touch sensor buttons of FIG. 6.

FIG. 7 depicts a cross sectional side elevation view of toothbrush handle portion 102 alone. Referring to FIGS. 1 and 7, handle portion 102 includes a top wall 181, bottom wall 182, and side walls 183 extending between the top and bottom. Top wall 181 may include a socket 180 configured for receiving a complementary configured stem 184 on head portion 104 (see, e.g. FIGS. 2A and 2B) for mounting the head portion to the handle portion. In one embodiment, socket 180 and stem 184 may have circular cross sections; however, any suitable cross sectional shape including rectilinear and polygonal shapes may be provided (e.g. square, hexagonal, triangular, etc.).

Figure 4:
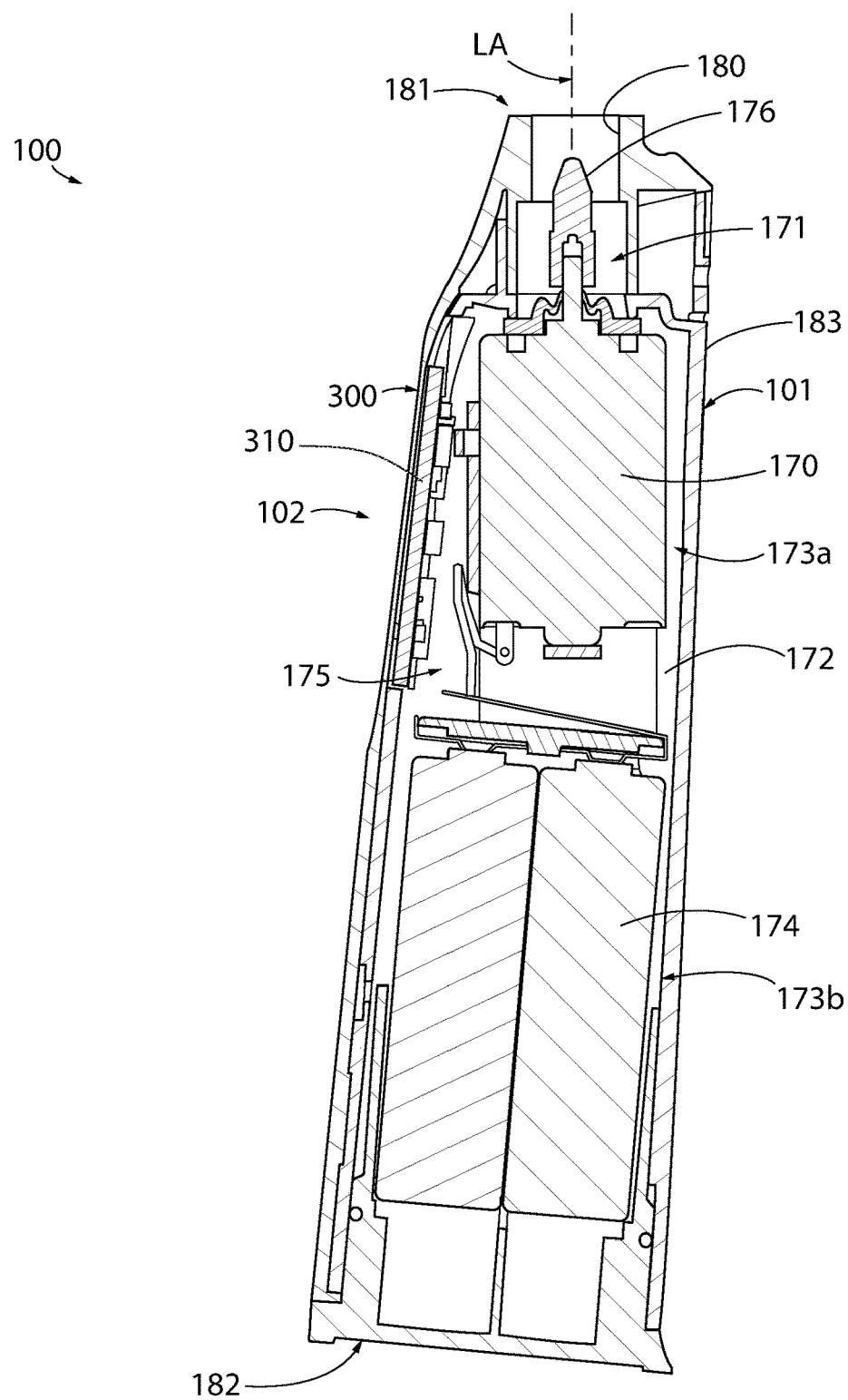
FIG. 4 is a side cross sectional view of the handle portion of toothbrush of FIG. 1.

Referring to FIGS. 1 and 4, handle portion 102 further includes an internal chamber 172 which defines a motor compartment 173a for supporting DC electric motor 170 and a battery compartment 173b configured for holding one or more batteries 174. Motor and battery compartments 173a, 173b may be contiguous or isolated from each other in chamber 172. Batteries 174 may be of any type including replaceable cells and/or rechargeable cells which are electrically connected to motor 170 via electrical connectors 175 which may include conductive contacts, wires, etc. Motor 170 includes a revolving rotor 171 have an end drive coupling 176 configured for detachable coupling to and driving a drive shaft 130 disposed in toothbrush head portion 104 (see, e.g. FIGS. 2A and 2B). Rotation of the motor rotor 171 in turn rotates the drive shaft 130 about its central axis CA. An operating panel 300 is provided which is electrically connected to motor 170 and includes switches or other type actuators for controlling on/off operation and/or speed of the motor.

Figure 2A:
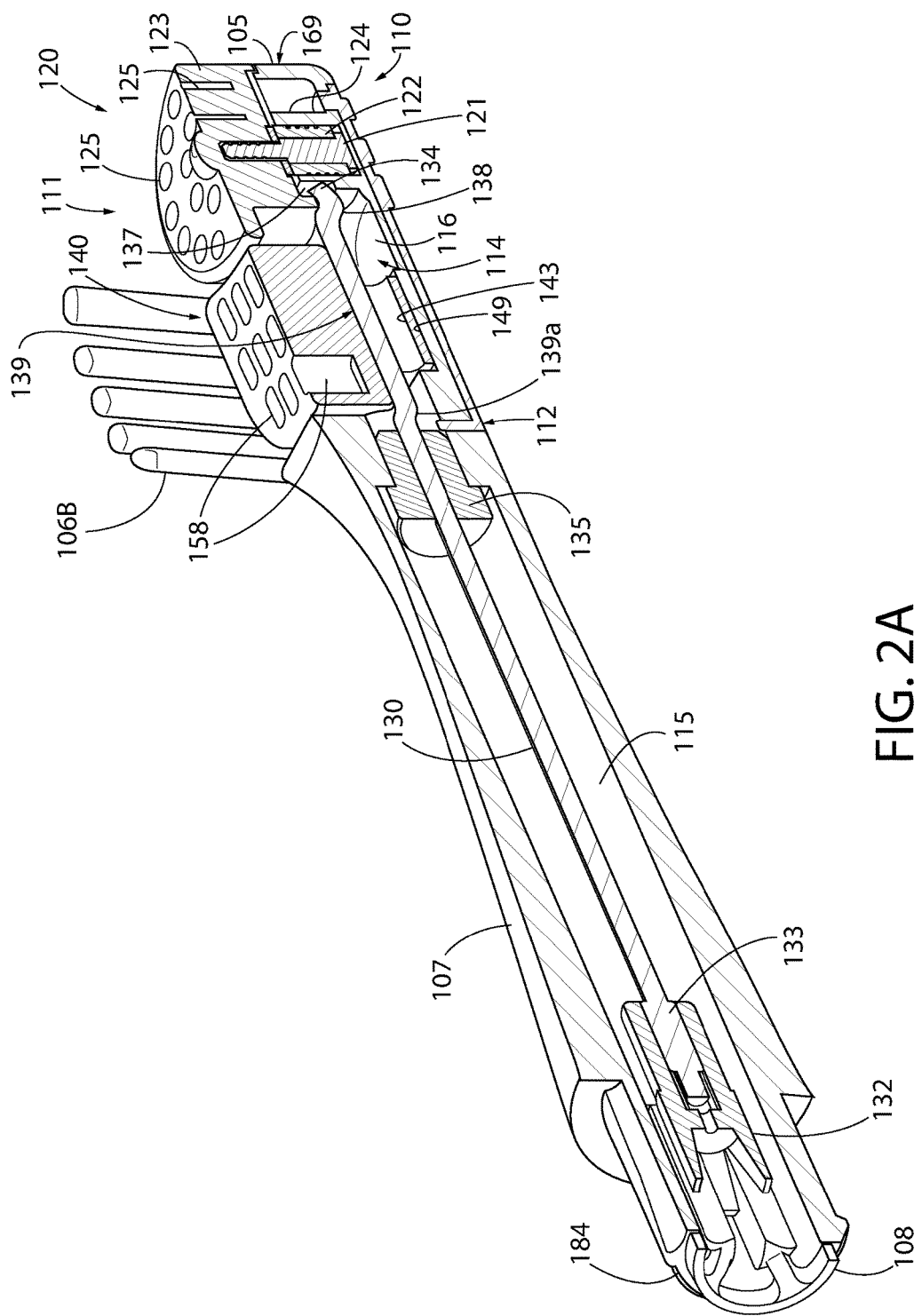
FIG. 2A is cross sectional perspective view of the head portion of the toothbrush taken along line IIA-IIA in FIG. 1.
Figure 2B:
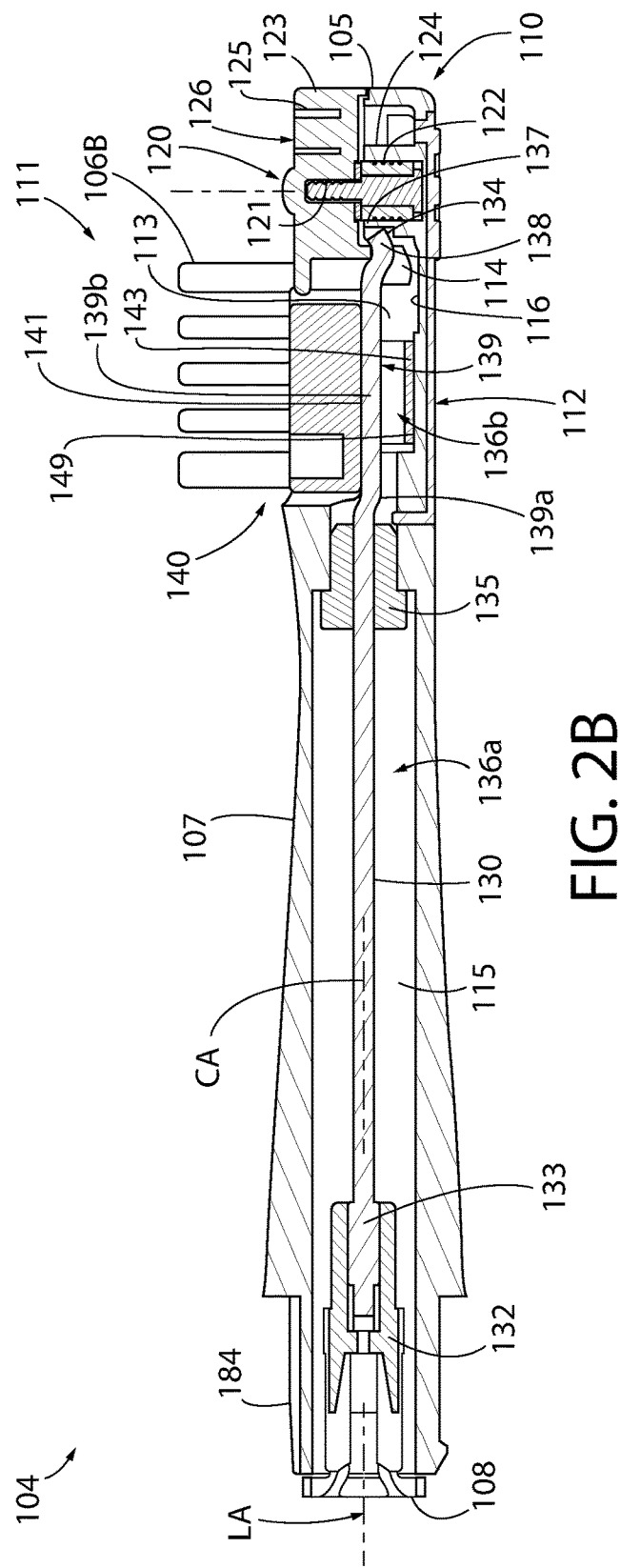
FIG. 2B is a side cross sectional view of the head portion of the toothbrush taken along line IIB-IIB in FIG. 1.
Figure 3:
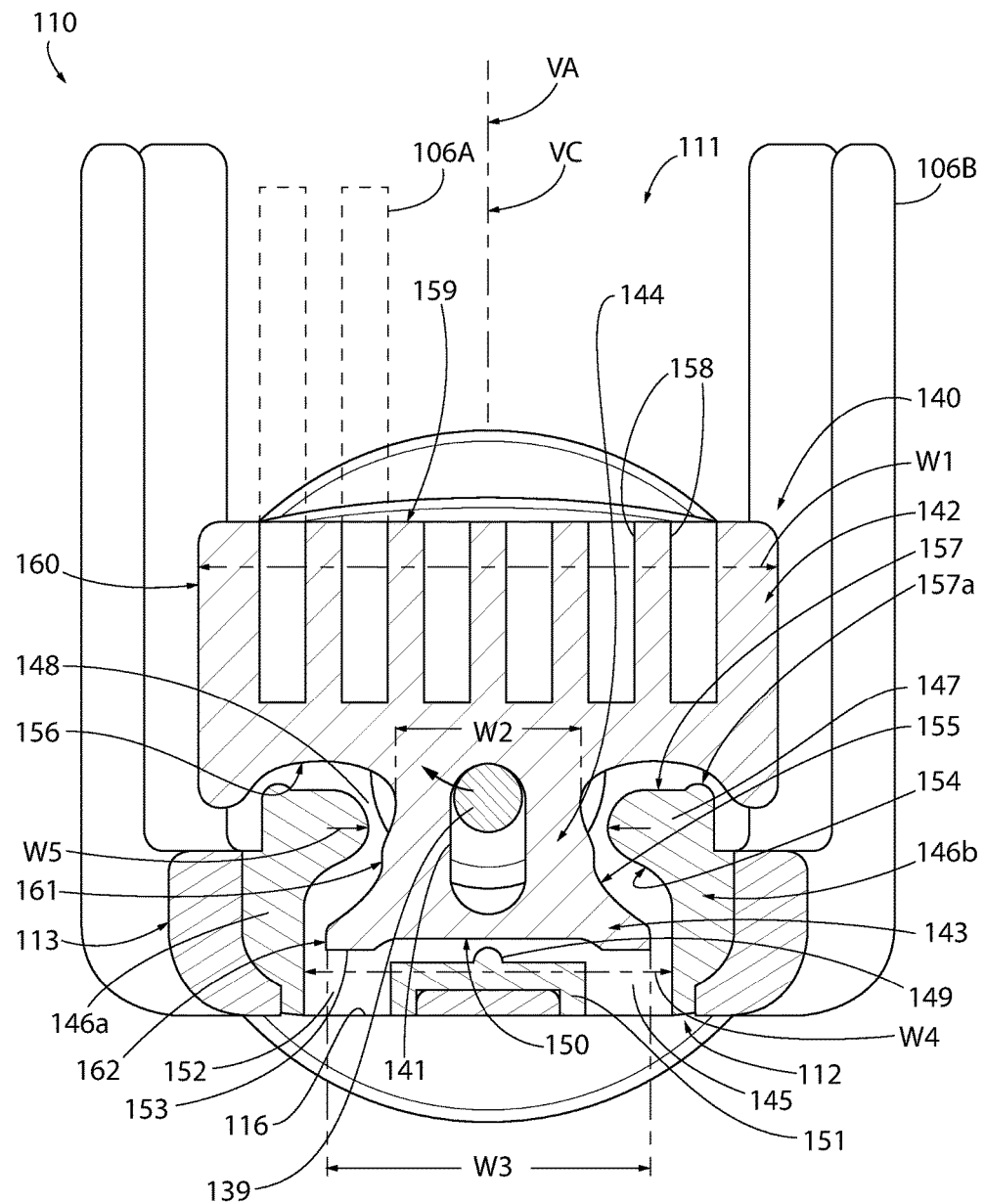
FIG. 3 is a transverse cross sectional view of a movable tuft block taken along line III-III in FIG. 1.

FIGS. 2A and 2B depict cross sectional perspective and side elevation views of toothbrush head portion 104 alone. FIG. 3 depicts a transverse cross section taken along line III-III in FIG. 1 through one of the tuft blocks 140. In one configuration, head portion 104 includes a head 110 and an elongated neck 107 connected to the head. Neck 107 defines an open proximal end 108 of head portion 104 lying along longitudinal axis LA opposite distal end 105 of toothbrush 100 which is defined by head 110. Proximal end 108 is configured for detachable mounting to a distal end 109 of the handle portion 102.

Toothbrush head 110 comprises a front side 111, an opposing rear wall 112, and opposing lateral side walls 113 extending around the periphery of the head. The rear and side walls 112, 113 define an internal cavity 114 which is open through the front side 111 of the head 110 and configured to receive tuft blocks 120, 140, as further described herein. Cavity 114 may therefore have a closed bottom surface 116 formed by rear wall 112 of head 110 and open top 117 facing and extending through the front side 111 of the head.

The rear walls 112 and lateral side walls 113 of head 110 can take on a wide variety of shapes and contours, none of which are limiting of the present invention. For example, these walls can be planar, contoured, or combinations thereof. Head 110 may be laterally widened in a direction transverse to longitudinal axis LA in contrast to neck 107 in some embodiments for supporting a variety of tooth cleaning elements 106.

In the exemplary embodiment, the neck 107 and head 110 of head portion 104 may be integrally formed as a single unitary structure using a molding, milling, machining and/or other suitable fabrication processes. However, in other embodiments the neck 107 and head 110 may be formed as separate components which are then connected at a later stage of the manufacturing process by any suitable technique known in the art, including without limitation thermal or ultrasonic welding, a tight-fit assembly, a coupling sleeve, threaded engagement, adhesion, or fasteners. Whether the head 110 and the handle 120 are of a unitary or multi-piece construction (including connection techniques) is not limiting of the present invention, unless specifically claimed.

Head 110 of toothbrush 100 is configured and structured to support a plurality and variety of different tooth cleaning elements 106 from the front side 111. As used herein, the term "tooth cleaning elements" is used in a broad generic sense to refer to any structure whatsoever that can be used to clean, polish, scrape, or wipe the teeth and/or soft oral tissue (e.g. tongue, cheek, gums, etc.) through relative surface contact. Examples of tooth cleaning elements that may be used include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient materials suitable for uses in an oral hygiene apparatus. The tooth cleaning elements 106 may be attached to head 110 by any suitable method used in the art. For example, without limitation, in-mold tufting (IFT) or anchor free tufting (AFT) could be used to mount the cleaning elements. Accordingly, invention is not limited by the types of tooth cleaning elements 106 provided or method of anchoring those elements to head 110 of head portion 104.

In one non-limiting embodiment, neck 107 may be generally tubular shaped having a circular and annular transverse cross section which may vary in diameter along the length of the neck in some configurations. Numerous other variations in the shape and configuration of neck 107 are possible. Neck 107 defines a longitudinally extending internal passageway 115 which extends through the neck from open proximal end 108 of head portion 104 into open cavity 114 formed in the head 110. Passageway 115 therefore communicates with cavity 114.

Referring to FIGS. 2A-B and 3, a drive shaft 130 is rotatably disposed inside head portion 104. Drive shaft 130 extends through internal passageway 115 from a point near proximal end 108 towards distal end 105 along longitudinal axis LA. In one embodiment, drive shaft 130 has a driven proximal section 136a disposed in neck 107 which may be substantially straight in one non-limiting embodiment and a working distal section 136b projecting into open cavity 114 of head 110 that is configured for operating movable tuft blocks 120, 140, as further described herein. Proximal end 133 of drive shaft 130 includes an adapter coupling 132 configured for detachably engaging drive coupling 176 of motor 170 disposed in handle portion 102 (see FIG. 7), thereby coupling the drive shaft to the motor. Rotation of the motor rotor 171 in turn rotates the drive shaft 130 about its central axis CA. In various embodiments, central axis CA may be concentrically aligned with or parallel to longitudinal axis LA. A bearing 135 may be disposed between the proximal and distal sections 136a, 136b of the drive shaft 130 near the conjuncture between the neck 107 and head 110 for supporting the drive shaft 130. This helps support the working distal section 136b against transverse or shear forces imposed on the drive shaft 130 when a user is brushing and presses the tooth cleaning elements 106A against their oral surfaces.

Toothbrush head 110 may include one or more powered movable tuft blocks 120 and 140 which are engaged by distal section 136b of drive shaft 130. Tuft blocks 120, 140 are each configured for mounting a plurality of moving tooth cleaning elements 106A thereto, as further described herein. Each shaft-driven tuft block 120, 140 may include tooth cleaning elements 106A in the form of bristles and/or elastomeric cleaning elements. Head 110 may further include non-motor-driven fixed or stationary tooth cleaning elements 106B in addition to any movable tuft blocks provided. The stationary tooth cleaning elements 106B may similarly include bristles and/or elastomeric cleaning elements. As used herein, the terms "movable" tuft blocks and "moving" tooth cleaning elements refers to tuft blocks and tooth cleaning elements which have motion produced via operation of a power drive (e.g. motor) without contact with a user's oral surfaces (e.g. teeth, gums, etc.) during brushing to impart movement. The terms "fixed" or "stationary" tooth cleaning elements refers to elements that are static when not in contact with a user's oral surfaces and move primarily only as a result of the tooth brushing action.

Referring to FIGS. 2 and 3, tuft block 120 may be a distal-most tuft block disposed near distal end 105 and end wall 169 of toothbrush head 110. In one embodiment, tuft block 120 may be an oscillating type tuft block as described U.S. Pat. No. 5,625,916, which is incorporated herein by reference in its entirety. Tuft block 120 is rotationally and arcuately movable back and forth in reversible directions through a limited arcuate path around a center support spindle 121 which is oriented transversely to longitudinal axis LA and defines an axis of rotation. Spindle 121 may be mounted in and supported by a suitable bearing 122 disposed in receptacle 124 formed inside cavity 114 to provide smooth rotational movement of the spindle. In some embodiments, a majority of tuft block 120 may be generally positioned in open cavity 114 formed in head 110.

In one embodiment, tuft block 120 is actuated and operated by a first angular offset segment formed by a curved or eccentric distal end 134 of drive shaft 130 which defines a first eccentric cam 138. Cam 138 may have a generally hooked configuration which includes a double bend having a first portion bent outwards away from the central axis CA of drive shaft 130 and a second portion bent back inwards towards the central axis CA. Cam 138 engages an operating slot 137 formed in a side of tuft block 120. Rotation of drive shaft 130 through 360 degrees oscillates or pivots tuft block 120 back and forth transversely to longitudinal axis LA of toothbrush 100 through an arcuate path of motion around spindle 121. In one representative but non-limiting example, the arcuate path of motion may be between about and including 10-90 degrees, and more particularly 20-30 degrees in some embodiments.

As shown in FIGS. 2A and 2B, tuft block 120 includes a plurality of openings 125 formed in an outward facing top surface 126 of an upper bristle holding portion 123 which are configured for inserting and mounting bristle tufts and/or elastomeric cleaning elements through the openings. Openings 125 may be of any suitable shape (in top plan view). Tuft block 120 may have any suitable configuration. In one non-limiting embodiment, tuft block 120 may have a circular shape in top plan view. Numerous other variations in shape are possible.

Referring initially to FIGS. 2A-B and 3, tuft block 140 in one non-limiting exemplary embodiment may be generally T-shaped or mushroom-shaped in transverse cross section. Toothbrush 140 includes an upper bristle holding portion 142, a lower base portion 143, and a narrowed reduced width intermediate portion 144 between portions 142 and 143. Bristle holding portion 142 has a vertical height sufficient for mounting bristles and/or elastomeric tooth cleaning members. A plurality of openings 158 formed in an outward facing top surface 159 of an upper bristle holding portion 142 are configured for inserting and mounting bristle tufts and/or elastomeric cleaning elements such as tooth cleaning elements 106A (illustrated in dashed lines) through the openings. Openings 158 may be any suitable shape (in top plan view). Top surface 159 extends transversely to longitudinal axis LA between the opposing lateral sides 160. In one embodiment, top surface 159 may be substantially flat; however, arcuately curved or undulating profiles may also be used. Tuft block 140 may be longitudinally elongated having a larger axial length (measured parallel to longitudinal axis LA) than lateral width measured between the lateral sides 160.

In one embodiment, bristle holding portion 142 has a width W1 which may be wider than width W2 of the intermediate portion 144 (measured at its narrowest point between lateral sides 161), and in some embodiments width W1 may be wider than width W3 of base portion 143 between lateral sides 162. Width W2 of intermediate portion 144 may be smaller than both widths W1 and W3 of bristle holding and base portions 142 and 143, respectively. This captures or traps the base portion 143 in a receptacle 145 formed within a portion of cavity 114 in toothbrush head 110 to prevent the tuft block 140 from being transversely extracted from the cavity through the front side 111 of the head, as further described herein.

Receptacle 145 may be formed and defined by opposing lateral walls 146a, 146b positioned in cavity 114 (see, e.g. FIG. 3). Walls 146a, 146b may be separate structures mounted inside the cavity 114 or may be formed by integral interior portions of lateral side walls 113 of the toothbrush head 110. In one embodiment, walls 146a, 146b may further define a pair of inward projecting operating flanges 147 which each extend towards longitudinal axis LA. Flanges 147 are spaced laterally/transversely apart to form a reduced width entrance 148 to receptacle 145 from front side 111 of toothbrush head 110. Entrance 148 has a lateral width W2 which is less than width W4 of receptacle 145. The free ends of flanges 147 may each have convexly curved or rounded surfaces to smoothly and slidingly engage tuft block 140, as further described herein. Portions of walls 146a, 146b below flanges 147 may be substantially vertical in one embodiment. The transition or shoulders 154 formed between flanges 147 and walls 146a, 146b may be concavely rounded to avoid sharp corners and provide a gradually contoured sliding surface configured to abuttingly and slidingly contact outwardly flared leg extensions 153 on base portion 143 of tuft block 140 for smooth movement.

A bottom portion of the receptacle 145 may further include an upwardly extending protuberance 149 formed above and generally proximate to and adjacent rear wall 112 of toothbrush head 110. Referring to FIGS. 2A-B and 3, protuberance 149 defines a pivot configured to engage a bottom surface 150 formed on base portion 143 of tuft block 140. In one embodiment, protuberance 149 may be generally shaped as a longitudinally extending ridge formed inside receptacle 145. In that configuration, protuberance 149 may have an axial length measured along the longitudinal axis LA which is substantially coextensive with the axial length of base portion 143 of tuft block 140 to restrict movement of the tuft block to a side-to-side lateral rocking motion and minimize rocking in a back and forth direction (i.e. proximal to distal) along the longitudinal axis LA. A ridge-shaped protuberance 149 may have a continuous or interrupted length and structure. Other variations in the shape and configuration of protuberance 149 however are possible. For example, in another possible embodiment, protuberance 149 may have a semi-spherical or half round shape (e.g. dimple or nub) with a limited axial length substantially less than the axial length of tuft block base portion 143.

In one embodiment, protuberance 149 may be formed on a raised pedestal 151 extending upwards from the bottom surface 116 of the cavity 114 within the confines of receptacle 145. Pedestal 151 may be a separate structure mounted inside the receptacle 145 or may be formed by integral interior portion of rear wall 112 of the toothbrush head 110. The pedestal 151 forms two pockets 152 on either lateral side for receiving laterally and outwardly flared leg extensions 153 on base portion 143 of tuft block 140 during movement of the tuft block. Leg extensions 153 extend laterally farther than intermediate portion 144 of tuft block 140.

Referring to FIG. 3, intermediate portion 144 may have generally concave curved lateral surfaces 155 for abuttingly and slidingly engaging the rounded flanges 147 formed in toothbrush head 110. This ensures smooth and unbinding motion as the tuft block 140 moves through its various positions, as further described herein. Similarly, the underside of upper bristle holding portion 142 of tuft block 140 may include concavely rounded bottom surfaces 156 contoured for smoothly engaging the top surface 157 of rounded flanges 147 formed in toothbrush head 110. The top surface may be configured to include raised longitudinally extending rails 157a to facilitate smooth non-binding contact with the underside surfaces 156 of the tuft block upper bristle holding portion 142.

In one embodiment, tuft block 140 is mounted on and actuated by a second angular offset segment formed by a curved or eccentric portion of drive shaft 130 which defines a second eccentric cam 139. Referring to FIGS. 2A, 2B, and 3, cam 139 is disposed between distal end 134 and proximal end 133 of drive shaft 130. In various embodiments, cam 139 may include at least one bend 139a as shown with an adjoining straight segment 139b having an axis which is transversely offset from and parallel to central axis CA of drive shaft 130. Cam 139 is configured and arranged to engage a vertically oriented and elongated operating slot 141 in tuft block 140 for moving the tuft block in a plurality of directions transverse to longitudinal axis LA of toothbrush 100 as the drive shaft 130 rotates. In one alternative embodiment, two bends 139a may be provided with offset straight segment 139b disposed therebetween.

It should be noted that in the embodiment shown in FIG. 3, none of the peripheral edges or sides of tuft block 140 are attached or coupled to toothbrush head 110 so that the tuft block is freely movable to translate in position vertically, laterally, and angularly (i.e. tilting) transverse to longitudinal axis LA when driven by drive shaft cam 139. This allows tuft block 140 to simulate a Bass brushing technique preferred by many oral care professionals. The sole point of coupling in the present embodiment between tuft block 140 and the toothbrush head portion 104 is via cam 139 engaging slot 141 formed in intermediate portion 144 of the tuft block. The range of vertical, lateral, and angular motion may be restricted by design via engagement between base and intermediate portions 143, 144 of tuft block 140 and flanges 147 formed in receptacle 145 of toothbrush head 110, as further described herein.

Tuft block 140 may be considered to define a vertical centerline VC extending vertically through the tuft block and oriented perpendicular to top surface 159 of the upper bristle holding portion 142 (see, e.g. FIG. 3). Vertical centerline VC is further defined as extending through drive shaft 130 and spaced equidistant between the lateral sides 160 of upper bristle holding portion 142. The vertical centerline VC is angularly movable with respect to vertical axis VA defined and fixed by toothbrush head 110. In FIG. 3, the vertical centerline VC is shown aligned with vertical axis VA when the tuft block 140 is in a vertically straight or upright orientation.

Tuft block 140 is driven or oscillates in an oscillation cycle produced by motor 170 through a lowermost bottom vertical position and an uppermost top vertical position via a combination of vertical raising/lowering, lateral, and tilting motions. In one embodiment, the oscillation cycle of brushing motion replicates the Bass brushing technique.

Referring to FIG. 3, the drive shaft 130 rotates in a clockwise direction and eccentric cam 139 rotates clockwise about the drive shaft to drive tuft block 140 through the oscillation cycle. Because the top (upper bristle holding portion 142), bottom (base portion 143), and lateral sides of tuft block 140 (i.e. lateral sides 160, 161, and 162) are not physically attached to the lateral side walls 113 or bottom wall 112 of toothbrush head 110 in which the tuft block is mounted, this free floating arrangement of tuft block 140 advantageously provides three degrees of motion not being constrained to simply vertical movement or pivoting movement about a fixed pivot axis alone. Accordingly, tuft block 140 is free to move angularly (i.e. rock or tilt), vertically, and laterally (horizontally) allowing an oscillation cycle of motion to be provided by a powered toothbrush that beneficially replicates compound brushing motions (e.g. Bass motion) normally achieved by manual brushing techniques.

Capacitive Touch Sensing Control

According to another aspect of the present invention, control panel 300 used to control the on/off operation and/or speed of the toothbrush 100 may include capacitive touch sensing technology in lieu of or in addition to mechanical switches.

Figure 5:
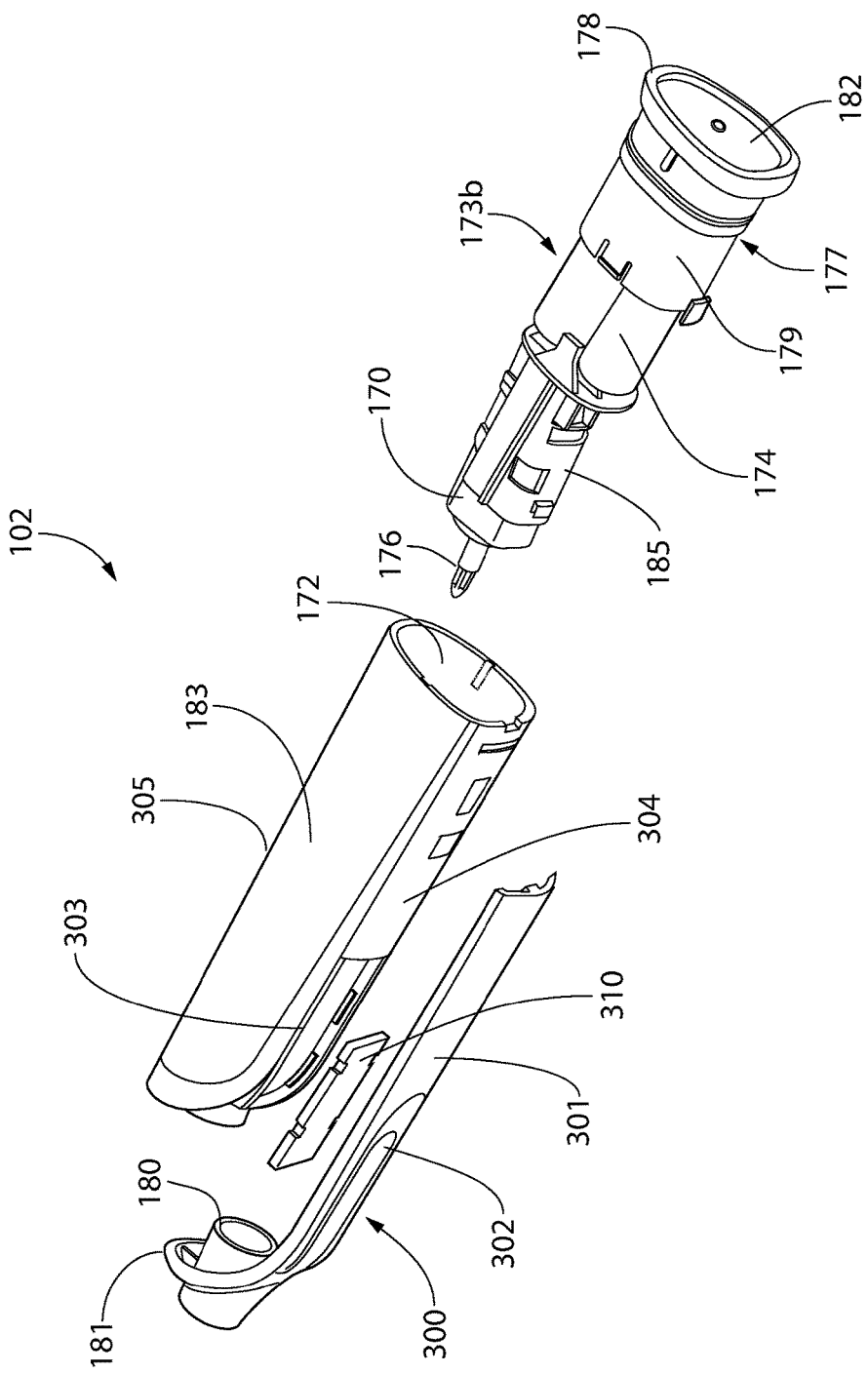
FIG. 5 is an exploded perspective view of another embodiment of a toothbrush including a handle portion incorporating a capacitive touch sensing control system.

FIG. 5 depicts an exploded perspective view of an exemplary embodiment of toothbrush 100 having a handle portion 102 which incorporates capacitive touch sensing technology. Features numbered similarly to FIGS. 1 and 7 are the same as previously described herein.

Referring to FIG. 5, the handle portion 102 may be constructed with a removable end cap assembly 177 providing a convenient access to battery compartment 173b for replaceable single use type batteries 174. End cap assembly 177 includes an end cap 178 which defines bottom wall 182 of handle portion 102 and tubular extension 179 configured for removably inserting and holding one or more batteries 172. In this embodiment, motor 170 may be mounted in a housing 185 which may be separate from or configured for attachment to end cap assembly 177. The motor housing 185 and end cap assembly 177 are insertable into downwardly open internal chamber 172 formed in handle portion 102. When mounted, end cap 178 closes the bottom of handle portion 102. Motor housing 185 and end cap assembly 177 may be retained in handle portion 102 by any suitable means known in the art.

Handle portion 102 includes a receptacle 303 configured for mounting a PCBA 310 (printed circuit board assembly) therein. Receptacle 303 opens through the front side 304 of handle portion 102 and communicates with internal chamber 172 to permit the passage and electrical connection of control wires from the PCBA 310 to the motor 170. PCBA 310 includes a capacitive touch sensor system, as further described herein.

With continuing reference to FIG. 5, front and rear portions of side walls 183 define a front side 304 and rear side 305. A detachable front face plate 301 may be provided in one embodiment which is configured for attachment to front side 304 by any suitable removable mechanical means (e.g. fasteners, snap fit, etc.) or non-removable mechanism means (e.g. adhesives, ultrasonic welding, etc.). In one embodiment, face plate 301 may be constructed to include front wall 181 of handle portion 102 and socket 180 which receives stem 184 of removable head portion 104 (see, e.g. FIGS. 2A and 2B). Front face plate 301 is configured to cover PCBA 310 and close the receptacle 303 when the face plate is mounted to the front side 304 of handle portion 102. Front face plate 301 may be formed of one or more materials. In one embodiment, front face plate may be formed of a suitable molded plastic material.

In one embodiment, front face plate 301 may include control panel 300. The control panel may be longitudinally elongated. Control panel 300 includes a thinned deformable actuation portion or panel 302 configured and structured to be elastically deformable and movable in response to applying an inward force F using light to moderate finger pressure. Actuation panel 302 functions to activate the capacitive touch sensor system for controlling operation of the toothbrush motor 170. Actual panel 302 may be formed by a deformable section of front face plate 310 having a thickness selected to be sufficiently thin and elastically deformable in response to a finger touch pressure to activate the sensor system. In one embodiment, actuation panel 302 may have a reduced wall thickness in comparison to adjacent thicker and stiffer portions of front face plate 301 intended for grasping rather than control of the toothbrush 100.

The deformable actuation panel 302 may be formed integrally with face plate 301 as part of a single unitary structure of the face plate or alternatively may be a deformable insert which is permanently affixed along its peripheral edges to the face plate in a complementary configured opening. Either type of construction is suitable. In the latter construction, actuation panel 302 may be formed of a different material than the face plate 301. For example, in one possible embodiment in which face plate 301 is made of a substantially rigid plastic material, operating panel may be formed of either thin metal or thin plastic of a type different than the adjacent thicker portions of face plate 301 and therefore more readily deformable to serve its intended function. Portions of front face plate 301 over the actuation panel 302 may be covered by an elastomeric overlay material such as TPE in some embodiments.

The capacitive touch sensor system will now be described in further detail. In one embodiment, the capacitive touch sensor system may be a metal over capacitance (MOC) type system which works on the principal of providing a pair of spaced part and electrically isolated conductors forming a capacitor and measuring the change of capacitance with a microprocessor that occurs when the spacing between the conductors is changed by a finger touch and deflection of one of the conductors. Suitable microprocessor-based capacitive touch sensor system devices are commercially available from suppliers such as Microchip Technology, Inc. of Chandler, Ariz.

Figure 6:
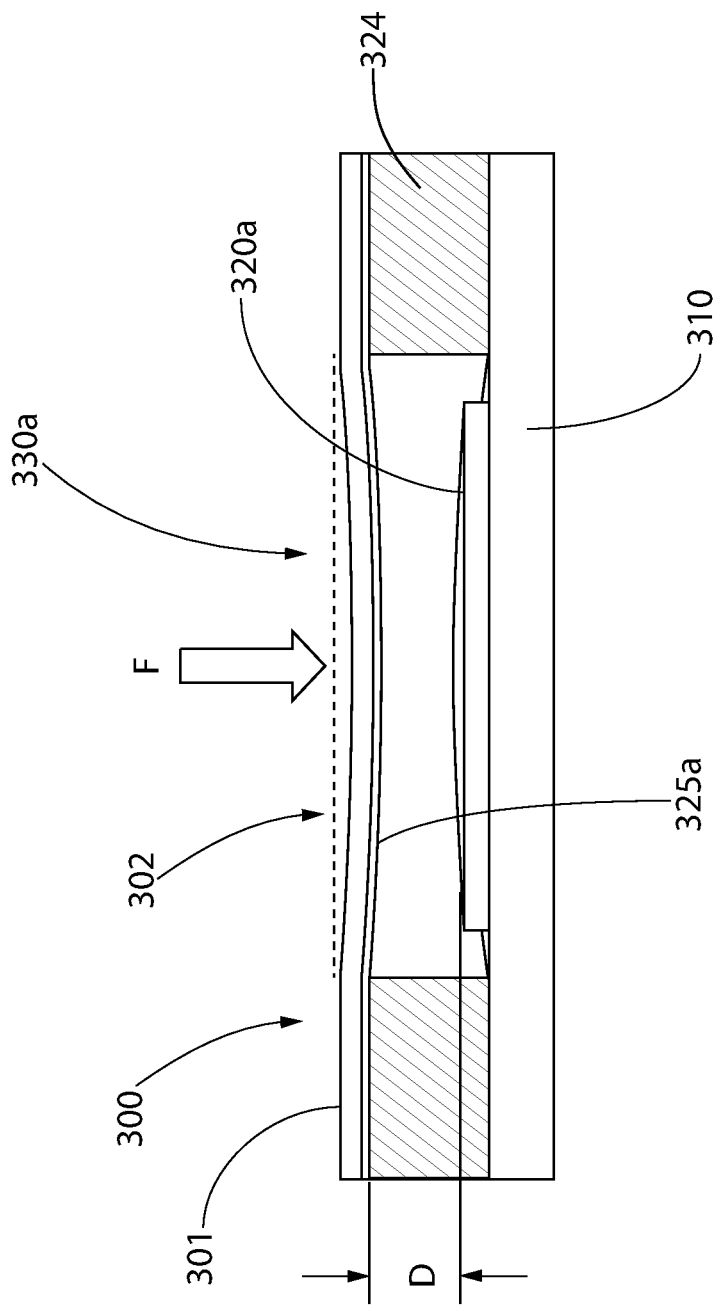
FIG. 6 is a side cross-sectional view of a capacitive touch sensor button including a pair of a movable sensor target and stationary capacitance sensor.

Referring now to FIGS. 6 and 7, an MOC capacitive touch sensor system includes an array of sensor buttons 330a-c each comprised of a conductive capacitance sensor 320a-c and a corresponding transversely aligned conductive sensor target 325a-c spaced apart therefrom and separated by a distance D. In one embodiment, sensors 320a-c and sensor targets 325a-c may be formed of an electrically conductive metal; however, various other conductive materials including without limitation conductive semiconductor materials may be used. Sensors 320a-c may be mounted on PCBA 310 and are electrically connected to and energized by a power source such as battery 174 creating a capacitance. Sensors 320a-c remain stationary with respect to PCBA 310 during operation of the control panel 300. By contrast, sensor targets 325a-c are movable during operation of the control panel transverse to longitudinal axis LA and attached to the underside of deformable operating panel 301. In one embodiment, sensor targets 325a-c may be formed by a thin metal film or layer affixed to the bottom (inner) surface of operating panel 301. The sensor buttons 330a-c are axially spaced apart along longitudinal axis LA and form electrically isolated discrete conductive elements which may be activated independently of each other by user touch.

Referring to FIGS. 6 and 7, spacer(s) 324 are provided between adjacent sensor buttons 330a-c which maintains physical separation (distance D) between sensors 320a-c and corresponding sensor targets 325a-c. The spacers 324 further isolate motion of each sensor button 330a-c from an adjacent button so that depressing a selected button and deflecting adjoining sensor target 325a-c via a finger touch to activate that sensor by changing distance D will not substantially change distance D in the adjacent unselected button which would render a false or errant unintended activation of the adjacent unselected button. Accordingly, the spacers 324 are preferably formed of a substantially rigid material to prevent deflection of the spacer during a finger touch/press action on actuation panel 302 and isolate the motion of each sensor button 330a-c so that the pressing force applied to one sensor button will not have a measurable effect on an adjacent button. Examples of suitable spacer materials are FR4 or non-deformable plastics. Adequate rigid mechanical support behind PCBA 310 is also preferably provided to prevent bending of PCBA substrate in the vicinity of sensors 320a-c to avoid loss of sensitivity. In some embodiments, spacers 324 may be formed by a continuous monolithic layer of spacer material with openings formed therein for each sensor button 330a-c or alternatively individual spacers. Either construction is acceptable; however, the former may be more cost effective.

Figure 8:
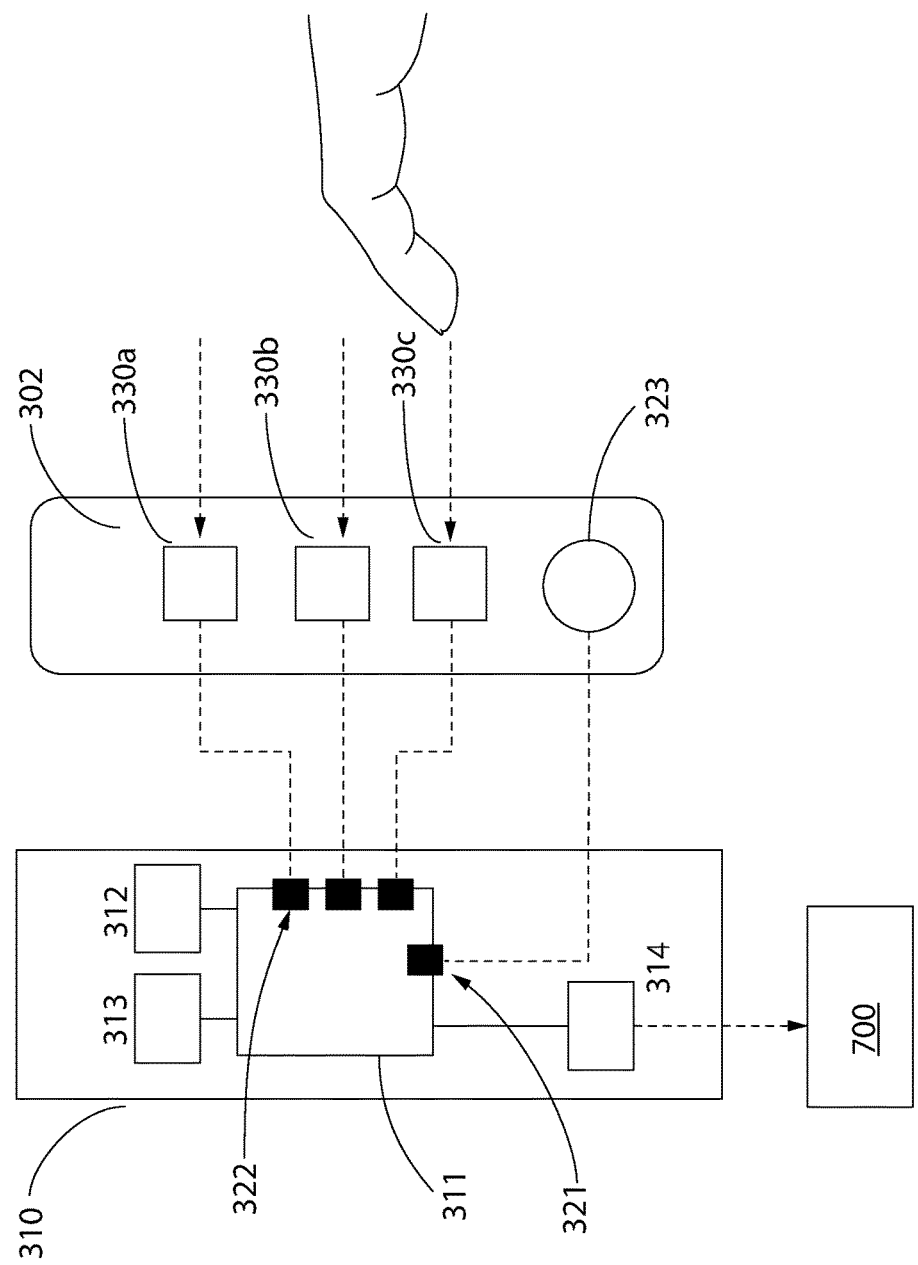
FIG. 8 is a schematic block diagram of the capacitive touch sensing control system.

Referring to FIGS. 7 and 8, the array of sensor buttons 330a-c in an exemplary non-limiting embodiment may include three sensor buttons arranged axially apart and linearly along the longitudinal axis LA of the toothbrush handle portion 102. This arrangement is convenient for a powered toothbrush 100 which generally has a relatively narrow handle in width (transverse to the longitudinal axis LA) for ease of grasping. Other suitable numbers of sensor button 330a-c may be provided in other embodiments. The sensor button array is designed to detect specific user gestures and sense the application of inward force or pressure by a user's digit (e.g. finger or thumb) against the deformable actuation panel 302 which are then translated by the software/firmware running on the microprocessor 311 to control the functions of toothbrush 100, such as turning the product on/off and varying the motor speed and hence brushing action.

FIG. 8 is a schematic diagram of the actuation panel 302 and PCBA 310 of the capacitive touch sensor system. The system includes a programmable microprocessor 311 mounted on the PCBA 310 which is configured controls the operation of the toothbrush motor 170 and toothbrush 100 in conjunction with the sensor buttons 330a-c which provide a user input device for controlling the microprocessor. Microprocessor 311 is configured to recognize touch activation by a user of a sensor button 330a-c via sensors 320a-c and executes program instructions via firmware and/or software configured to direct the operation and control of toothbrush 100. In addition to microprocessor 311, the capacitive touch sensor system includes all other peripheral devices and components necessary to form a fully functional programmable data processing system as will be known to those skilled in the art. This may include without limitation suitable volatile and non-volatile memory 312 (e.g. RAM, ROM, etc.), timer 313 such as electronic and/or software timers, analog capacitance-to-digital converter, digital signal controllers, compensation circuitry, processor registers, peripheral interfaces, real time clock (RTC), non-transitory machine readable medium, circuits and data buses, input/output interfaces, drivers (e.g. display, LEDs, audio, etc.) and others. Batteries 174 may provide the power supply for microprocessor 311. Microprocessor 311 is configured and operable to convert the capacitance detected by sensors 320a-c into a digital value further manipulated by the microprocessor to direct operation of the toothbrush 100.

Sensitivity control is programmed into microprocessor 311 for touch detection in the form of a threshold capacitance value Ct to distinguish between an unintended soft touch on deformable actuation panel 302 and a harder touch intended to activate sensors 320a-c. This ensures that only a positive, intended harder touch is detected versus mere grasping and handling of the toothbrush 100 by a user. Accordingly, the microprocessor 311 may be programmed with a threshold capacitance detection value Ct which must be met or exceeded (correlated to the degree of deflection of the sensor target 325a-c by a user) before control of the toothbrush operation is implemented by the microprocessor.

Referring to FIG. 8, the sensors 320a-c associated with sensor buttons 330a-c are each connected to dedicated input ports 322 (e.g. pins, pads) on microprocessor 311 via conductive communication traces or links (dashed lines) which transmit measured capacitance signals from each button to the microprocessor for detecting a user touch event. In one embodiment shown, one of the sensor buttons 330a, 330b, or 330c may serve a dual function of controlling on/off operation of the toothbrush 100 via programming microprocessor 311 in addition to having an associated motor operating speed. In other possible embodiments, a separate on/off switch 323 may be provided which may be a capacitance touch sensor button similar to sensor buttons 330a-c or another type of switch (e.g. mechanical, etc.) which is operably linked to a separate input port 321 on the microprocessor 311 via a conductive communication trace or link (dashed line). In other embodiments, the on/off switch may be a mechanical type switch which is not controlled by microprocessor 311 and instead is directly electrically coupled to the motor 170 via an electrical circuit for controlling the toothbrush on/off operating function. With a separate on/off switch, the sensor buttons 330a-c may be used for only controlling the speed of motor 170 after the toothbrush 100 has been turned on.

Motor 170 may be a DC variable speed motor in which the MOC capacitive touch sensor system controls the rotational speed (RPM) of rotor 171 to vary the oscillation rate of the movable tuft blocks 120, 140. Variable speed operation may be accomplished by any suitable means used in art, including without limitation a motor speed controller 314 (see FIG. 11) such as an electronic speed controller (ESC) or a pulse width modulation (PWM) controller, both of which include appropriately configured electronic circuitry and devices (e.g. MOSFETs, oscillators, resistors, capacitors, etc.) configured to control the power supplied to motor 170 and hence its speed. Such DC motor speed control devices are commercially available. In one embodiment, these devices may be incorporated onto PCBA 310. The MOC capacitive touch sensor system is operably connected to and controls operation of the electronic speed controller.

Operation of the toothbrush 100 and present capacitive touch sensing control system will now be described in further detail. According to one aspect of the invention, microprocessor 311 may be programmed and configured so each of the sensor buttons 330a-c act as a discrete switch for changing the speed (RPM) of motor 170 and/or turning the toothbrush on or off. Accordingly, touching a specific location on the control panel 302 associated with one of the sensor buttons 330a-c changes speed of the motor 170 to a specific speed assigned to that button, thereby concomitantly changing the oscillating rate of tuft blocks 120, 140. Any specific speed S1, S2, S3 may be assigned to each one of the sensor buttons 330a-c (e.g. low, medium, and high) for three speed operation. More or less speeds may be provided such as by furnishing more or less sensor buttons 330a-c, or alternatively programming the microprocessor 311 to associate each sensor button with activating more than one speed. Accordingly, the invention is expressly not limited to the number of sensor buttons or speeds described herein which represent merely some non-limiting examples.

In one arrangement, the user may skip to any one of the specific speeds S1, S2, S3 immediately by depressing the control panel 302 at a specific sensor button 330a-c location without going through any interim speeds. Accordingly, in one example, a user may skip from S1 to S3 or S3 to S1 by pressing on the respective sensor buttons 330a, 330b, or 330c.

A method or process 900 for controlling operation of toothbrush 100 will now be described with respect to a toothbrush 100 having two sensor buttons 330a and 330b. In one embodiment, the microprocessor-based control process 900 may be used to cycle toothbrush 100 through three different operating modes including an initial mid-speed mode, high max-speed mode, and a pulse mode by activating one or more of the sensor buttons 330a-b as described below.

Figure 9A:
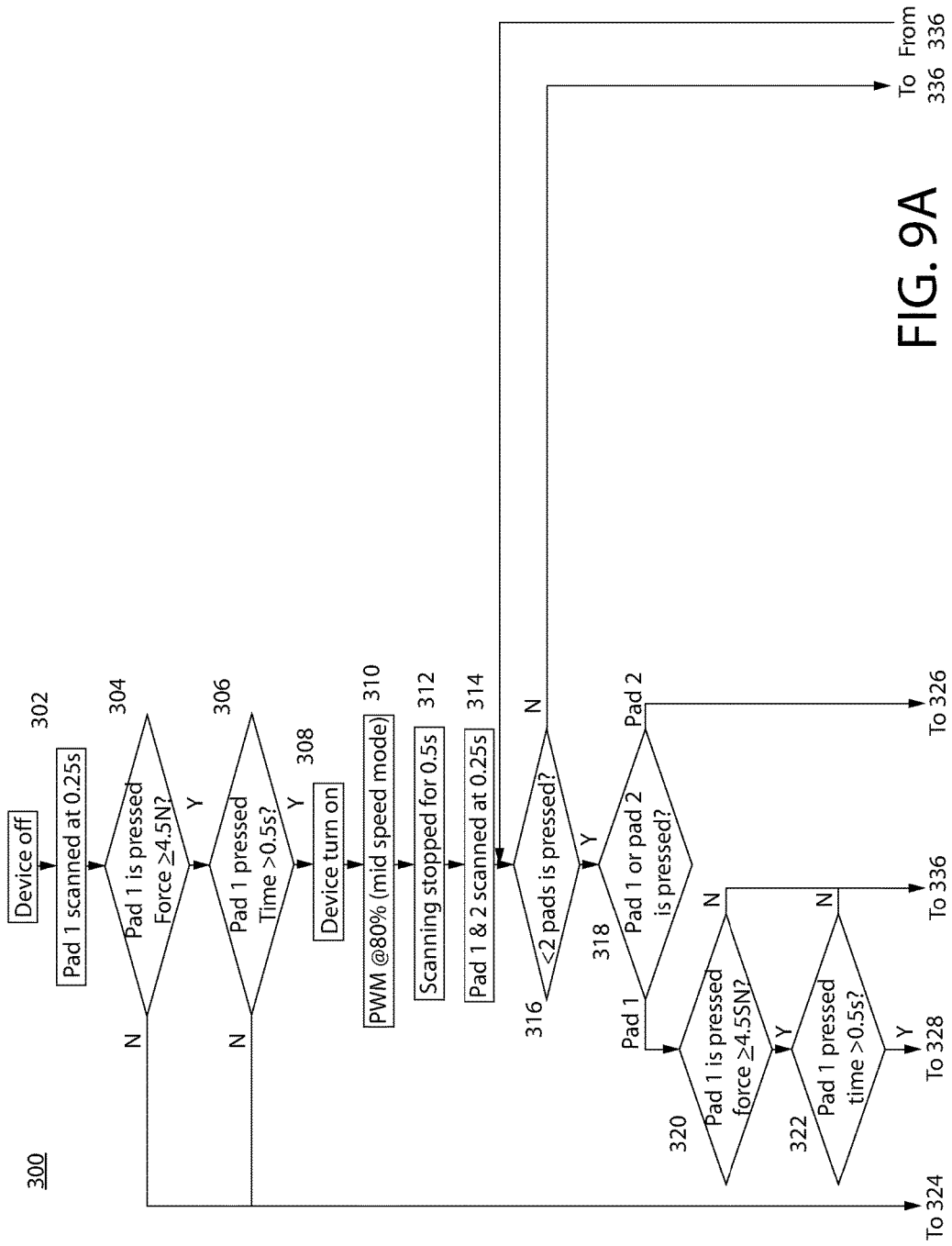
FIG. 9A-B is a flow chart of an exemplary process for controlling a powered toothbrush apparatus.
Figure 9B:
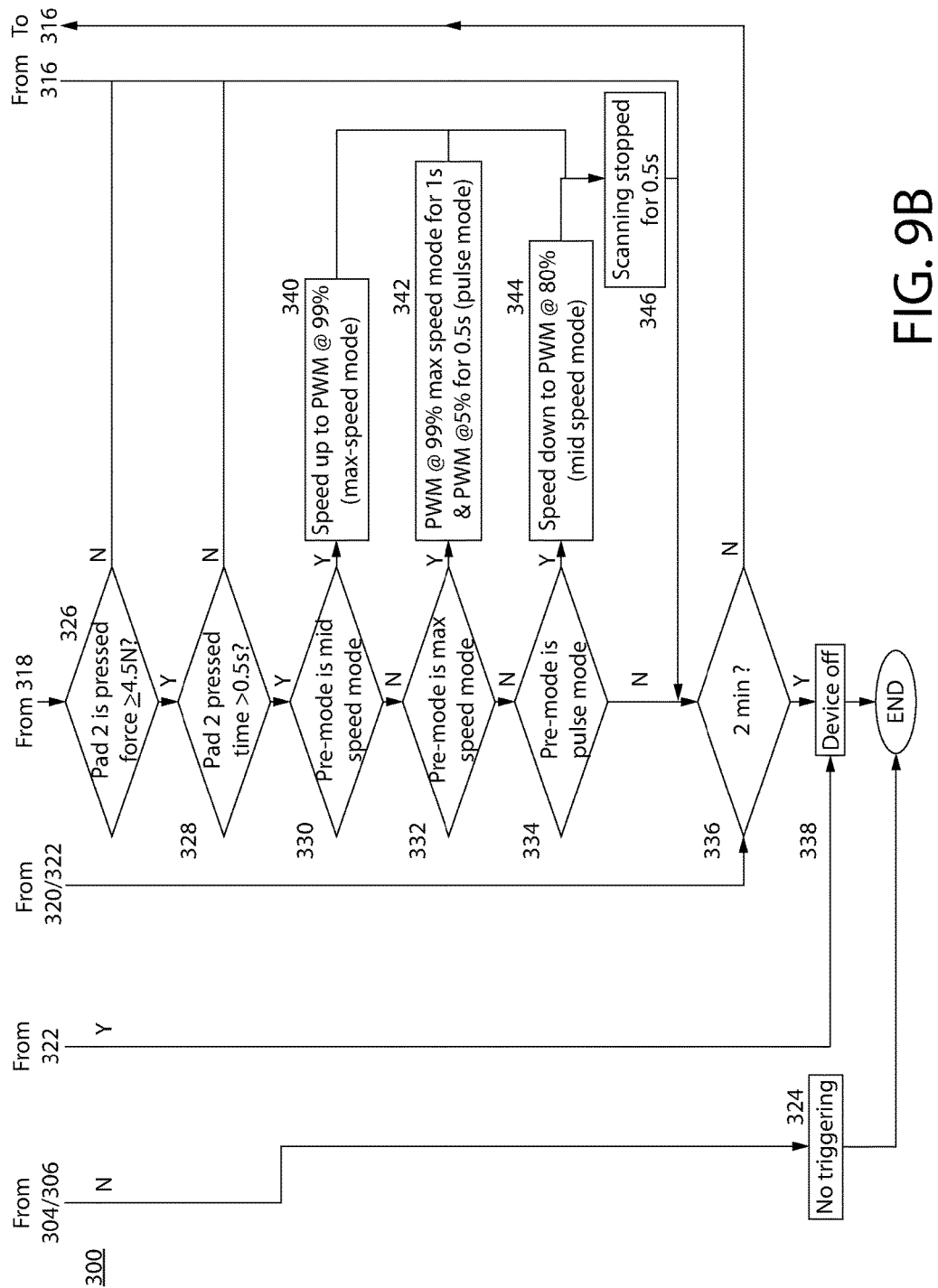

FIG. 9A-B is a logic flow chart depicting control process 900 executed by an appropriately programmed microprocessor 311 utilizing the MOC capacitive touch sensor system disclosed herein for controlling operation of powered toothbrush 100. The microprocessor 311 is programmed in the single-button operating mode described above to recognize individual or discrete activation of each sensor button 330a-b (e.g. one at time) via pressing or touching actions applied by a user against deformable actuation panel 302 of the control panel 300. The microprocessor 311 may further be programmed to recognize a "press and hold" pressing action in which one of the sensor buttons 330a or 330b is held down by a user for at least a period of time greater than a preprogrammed time duration limit.

The steps of process 300 shown in FIG. 9A-B are performed by microprocessor 311 executing program instructions triggered by and in response to finger or thumb pressing touches by a user on a specific location of control panel 300 associated with one of the sensor buttons 330a and 330b. The touching action changes the capacitance of and activates the respective sensor button which operates to change speed (RPM) of motor 170 and/or turn the toothbrush 100 on or off.

In control process 300 to be described, it should be noted toothbrush 100 and capacitive touch sensor system In FIG. 9A-B, sensor buttons 330a is alternatively referred to as "pad 1" and sensor button 33b as "pad 2" for brevity to not unduly clutter the figure.

Referring now to FIG. 9A-B, process 300 begins in step 302 with microprocessor 311 scanning sensor button 330a (pad 1) to detect a possible change in capacitance thereby indicating a user touching or pressing action on the button. Sensor button 330a (pad 1) may be continuously monitored or scanned every 0.25 seconds or another appropriate interval of time by microprocessor 311 for detecting an activation touch by the user.

In decision step 304, the microprocessor 311 determines whether sensor button 330a (pad 1) has been pressed with sufficient force by a user to indicate intentional activation versus merely inadvertent touching in routine handling of the toothbrush. In one representative non-limiting example, a threshold pressing force Ft of 4.5N may be preprogrammed into microprocessor 311 which must be met or exceeded to indicate a positive pressing or touching action on sensor button 330a (pad 1) by a user to activate the toothbrush. Other suitable threshold pressing forces may be used. If the actual pressing force F measured is less than the threshold pressing force Ft (i.e. "no" response), then no triggering action is taken by the microprocessor. If the actual pressing force F measured is greater than or equal to the threshold pressing force Ft (i.e. "yes" response), control passes to step 306. It should be noted that the change in capacitance associated with the amount of deflection created by pressing on deformable actuation panel 302 at sensor button 330a (pad 1) may be correlated to pressing force F which in turn may be programmed into the microprocessor for comparison with the preprogrammed threshold pressing force Ft to accomplish the foregoing functionality. Other suitable approaches, however, may be used.

With continuing reference to FIG. 9A-B, in decision step 306 the microprocessor 311 determines if sensor button 330a (pad 1) has been pressed for longer than a predetermined "hold time" programmed into the microprocessor for turning the toothbrush 100 on. This may be referred to as a "press and hold" action by the user. In one non-limiting example, the hold time may be 0.5 seconds. Other suitable times may be used. If the answer is "no" in step 306, then no triggering action is taken by the microprocessor. If the answer is "yes", control passes to step 308 and the toothbrush motor 170 is turned on by the microprocessor. In this example, the motor speed controller 314 may be a pulse width modulation (PWM) controller as described above.

The motor 170 speed may be ramped up to an initial or starting motor speed S1 in step 310. In one non-limiting example, the PWM programmed into microprocessor 311 which is associated with activation of sensor button 330a (pad 1) may be set at 80% to operate motor 170 initially when toothbrush 100 is first turned on at a "mid-speed mode" representing 80% of the maximum motor speed. Tuft blocks 130 and 140 will oscillate at a corresponding first rate associated with an 80% PWM. Other suitable initial PWM % or motor speeds may be used in other embodiments.

In step 312, scanning may be temporarily stopped for a predetermined period of time (e.g. 0.5 seconds or other) after starting the motor 170, thereby creating a brief pause to ensure another control action is implemented by the user before the control system can properly adjust operation. In step 314, both sensor buttons 330a (pad 1) and 330b (pad 2) are then scanned by microprocessor 311. The microprocessor 311 next determines if less than 2 sensor controls buttons (pads) are pressed in decision step 316.

In decision step 316, if the microprocessor 311 determines that 2 sensor buttons 330a (pad 1) and 330b (pad 2) have been pressed (i.e. "no" response), control passes to decision step 336. If the toothbrush has been turned on for more than a predetermined brushing time duration programmed into microprocessor 311 (i.e. a "yes" response), control passes to step 338 and the microprocessor turns the toothbrush 100 off. If alternatively a "no" response is returned, control passes back to step 316 for continued tooth brush operation. In one representative example, the predetermined brushing time duration programmed into microprocessor 311 may be about 2 minutes which is a commonly recommended minimum duration for brushing the teeth. Other suitable brushing times may be used.

In decision step 316, if the microprocessor 311 determines that a single sensor button 330a (pad 1) or 330b (pad 2) has been pressed (i.e. "yes" response), control passes to decision step 318. In step 318, the microprocessor 311 determines whether sensor button 330a (pad 1) or sensor button 330b (pad 2) has been pressed. If sensor button 330a (pad 1) has again been touched, the microprocessor 311 in step 320 determines whether the actual pressing force F meets or exceeds the preprogrammed threshold pressing force Ft indicating an intentional "pressing" action. If the response is "no," If alternatively in step 320 the response is "yes," control passes to decision step 322. In step 322, the microprocessor determines if sensor button 330a (pad 1) has been pressed for longer than a predetermined "hold time" ("press and hold" user action) programmed into the microprocessor (e.g. 0.5 seconds or other). If the response is "no," control passes to step 336 to determine whether the predetermined brushing time duration (e.g. 2 minutes) programmed into microprocessor 311 has been met as described above to either turn the tooth brush off (step 338) or leave the toothbrush running as described above. If alternatively in step 322 the response is "yes," the microprocessor 311 automatically turns the toothbrush 100 and motor 170 off since a "press and hold" action by the user on sensor button 330a (pad 1) functions to turn the tooth brush alternatingly both on and off.

Returning to decision step 318, if sensor button 330b (pad 2) has been touched after starting the toothbrush 100, control passes to decision step 326. In step 326, the microprocessor both if sensor button 330b (pad 2) has been pressed with a sufficient pressing force F that equals or exceeds the threshold pressing force Ft. If the response is "no," control passes to step 336 to determine whether the predetermined brushing time duration (e.g. 2 minutes) programmed into microprocessor 311 has been met as described above to either turn the tooth brush off (step 338) or leave the toothbrush running as described above. If the response is "yes," control passes to step 328.

In decision step 328, microprocessor 311 determines if sensor button 330b (pad 2) has been pressed for longer than a predetermined "hold time" ("press and hold" user action) programmed into the microprocessor (e.g. 0.5 seconds or other). If the response is "no," control passes to step 336 to determine whether the predetermined brushing time duration (e.g. 2 minutes) programmed into microprocessor 311 has been met as described above to either turn the tooth brush off (step 338) or leave the toothbrush running as described above. If the response is "yes," control passes to step 330.

Control steps 330, 332, and 334 further change the operating mode of toothbrush 100 based on sequential additional pressing actions on sensor button 330b (pad 2). Continuing first now with decision step 330, the microprocessor 311 determines whether the present operating mode of the toothbrush 100 is the mid-speed mode (i.e. PWM @80%). If the response is "yes" indicating toothbrush 100 is presently in mid-speed mode, control passes to step 340 which increases the motor speed to "maximum speed mode" corresponding to a PWM @99% of the maximum motor speed. Control then passes to step 346 which may temporarily stop scanning for a period of time (e.g. 0.5 seconds or other) thereby creating a brief pause to ensure another control action is implemented by the user before the control system can properly adjust operation. Control then passes to decision step 336 for further processing as already described herein.

If the response is "no" in step 330, control passes to decision step 332 in which the microprocessor 311 determines whether the present operating mode of the toothbrush 100 is the high max-speed mode (i.e. PWM @99%). If the response is "yes" indicating toothbrush 100 is presently in max-speed mode, control passes to step 342 which initiates a "pulse" mode. The max-speed mode of motor 170 is maintained and motor 170 is alternatingly cycled between a longer first pulse time duration TP1 at 99% PWM (maximum speed) and a shorter second pulse time duration TP2 at a reduce speed less than maximum speed. In one exemplary non-limiting embodiment, TP1 may be 1 second at 99% PWM and TP2 may be half of TP1 or 0.5 seconds at a reduced speed which may be 5% PWM or other. In other embodiments, the reduced speed may be mid-speed mode (PWM@80%). It will be appreciated that numerous other suitable time durations TP1, TP2 and respective motor operating speeds may be used. Control then passes to step 346 which may temporarily stop scanning for a period of time (e.g. 0.5 seconds or other) thereby creating a brief pause. Control then passes to decision step 336 for further processing as already described herein.

If the response is "no" in step 332, control passes to decision step 334 in which the microprocessor 311 determines whether the present operating mode of the toothbrush 100 is the pulse mode. If the response is "yes" indicating toothbrush 100 is presently in pulse mode, control passes to step 344 in which microprocessor 311 reduces or slows down the motor speed to the mid-speed mode (PWM@80%). Control then passes to step 346 which may temporarily stop scanning for a period of time (e.g. 0.5 seconds or other) thereby creating a brief pause. Control then passes to decision step 336 for further processing as already described herein.

If the response is "no" in step 334, control passes to decision step 336 for further processing as already described herein to determine if the toothbrush 100 has been operating for the predetermined brushing time duration programmed into microprocessor 311 (e.g. 2 minutes or other). If the toothbrush has been turned on for more than a predetermined brushing time duration programmed into microprocessor 311 (i.e. a "yes" response), control passes to step 338 and the microprocessor turns the toothbrush 100 off. If alternatively a "no" response is returned, control passes back to step 316 for continued tooth brush operation.

In the foregoing operating scenario of toothbrush 100, sensor button 330a (pad 1) and sensor button 330b (pad 2) essentially provide two-button operation with sensor button 330a (pad 1) functioning in a "press and hold" mode for turning the toothbrush on and off. Sensor button 330b (pad 2) functions as a speed and pulse mode control button allowing the user to cycle the toothbrush between mid-speed and high-speed modes and pulse mode, as described above. In other embodiments contemplated, three button operation may be provided for example where sensor button 330b (pad 2) may provide inputs to the microprocessor 311 for changing speed between the mid-speed and max-speed modes (or additional speeds that could be provided) and the third sensor button 330c may be programmed for the microprocessor to turn the pulse mode on or off at any of the present operating speeds associated with sensor button 330b (pad 2). Numerous other variations and configurations of operating modes and functionality may be provided and programmed into microprocessor 311.

It will therefore be appreciated that although above process 900 was described with respect to a two sensor button array and operation, three or more sensor button operation may be provided in other embodiments using a similar methodology. In addition, additional two button operating modes may be provided such as mid-speed pulse mode using a similar methodology. Accordingly, the invention is expressly not limited to the non-limiting two button operation or It will further be appreciated that the exposed outer surface of control panel 300 may or may not include indicia or markings indicating the locations of the sensor buttons 330a-c beneath the capacitive touch deformable actuation panel 302 to a user. In one embodiment, markings are provided. However, the actuation panel 302 may be plain or unmarked in other embodiments. Either of the foregoing approaches to marking may therefore be used with the present invention.

Figure 10:
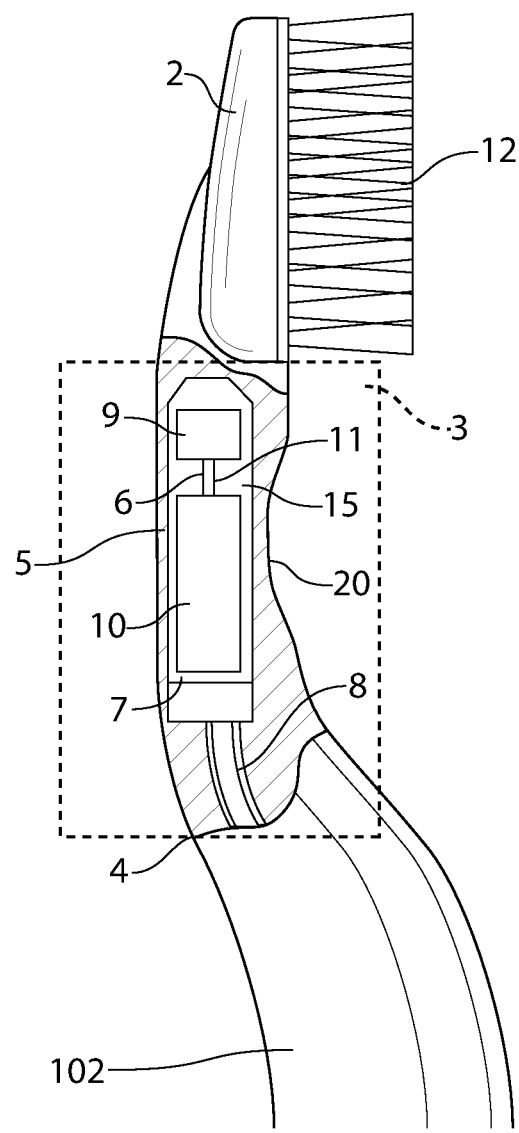
FIG. 10 is a side cross-sectional view of a head and neck portion of a vibrating sonic type toothbrush having a head to which vibrations are imparted, and incorporating a capacitive touch sensing control system.

FIG. 10 shows an exemplary embodiment of a vibrating sonic type toothbrush which may also be controlled using the MOC capacitive touch sensor system described herein. Such toothbrushes are described in U.S. Pat. No. 7,886,393, which is incorporated herein by reference in its entirety. The vibrating toothbrush of FIG. 10 generally comprises a handle which may be handle portion 102 containing the capacitive touch sensor system, a cleaning head 2 usually having cleaning elements 12, and a neck 3 disposed between the head 2 and the handle 1. While the cleaning head 2 illustrates bristles 12, other cleaning elements of various size, cross-section, material, etc., such as rubber elements, elastomeric elements, polishing elements, abrasive elements, floss-like cleaning elements, etc., may be used. The head 2 and neck 3 are usually formed of a relatively stiff material, such as polypropylene (PP), although other materials may be used. However, such material is also relatively elastic such that the neck and head can vibrate during use.

The neck 3 contains a mechanical vibratory device 5 that preferably includes a motor 10 and a vibratory element such as an eccentric weight 9 connected thereto by a shaft 11. By methods well known in the art, the vibratory device 5 can be connected to a power source such as an electrical power source such as battery 174 disposed in handle portion 102 via electrical connections 8 provided in the neck 3, and activated by deformable actuation panel 302 which includes the user touchable capacitive sensor buttons 330a-c (see also FIGS. 6-8). Alternatively, the power source can be located outside of the toothbrush, such as with direct current via a wall socket connection. In addition, the neck 3 can be formed as a unitary structure with the head 2 and handle 1 such as by injection molding or the like, or it can be separable from the handle 1 (not shown) preferably along location 4.

The mechanical vibratory device 5 produces vibrations in the head 2 through rotation of the eccentric weight 9 about the shaft 11. The motor 10 and eccentric weight 9 are preferably accommodated in a structural housing 15, which is preferably positioned in the neck 3 adjacent the head 2. The vibrations produced occur nearest the eccentric weight 9, which is positioned closer to the head 2 than the motor 10, which is closer to the handle 1 than the head 2. As noted above, the neck 3 is preferably made of an elastic material which facilitates the transmission of the vibrations from the weight 9 to the head 2. Of course, the mechanical vibratory device 5 can be positioned in a location that is not adjacent the head 2 as shown, as long as there are means to transmit the generated vibrations to the head 2.

Figure 11:
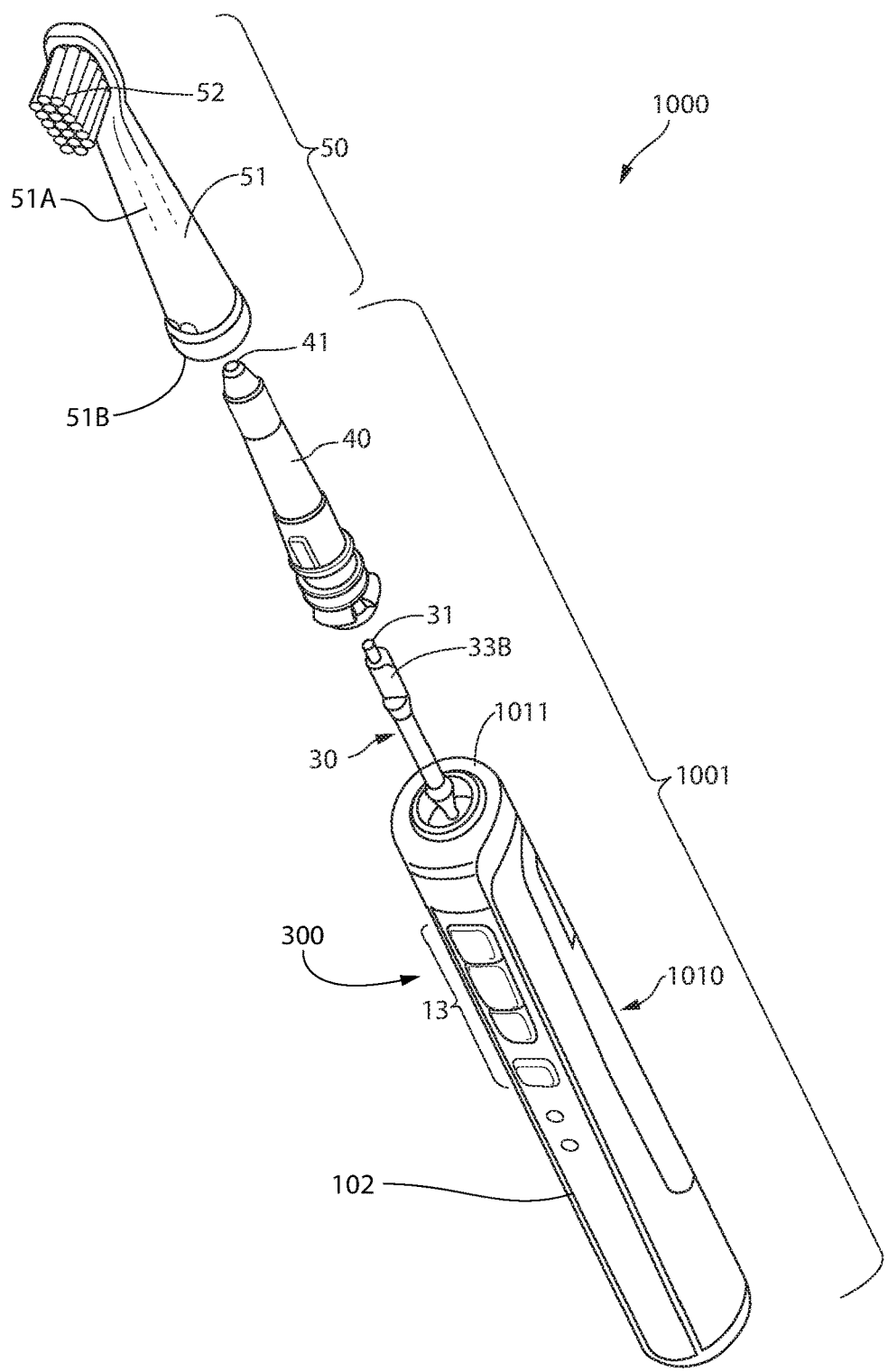
FIG. 11 is a perspective view of a vibrating sonic type toothbrush having a replaceable heads, and incorporating a capacitive touch sensing control system.

FIG. 11 shows an exemplary embodiment of a vibrating sonic type toothbrush having replaceable heads which may also be controlled using the MOC capacitive touch sensor system described herein. Such toothbrushes are described in PCT International Patent Application No. PCT/US2012/042973 filed Jun. 18, 2012, which is incorporated herein by reference in its entirety. The vibrating toothbrush of FIG. 11 generally comprises a handle which may be handle portion 102 containing the capacitive touch sensor system. Electric toothbrush 1000 includes an electric toothbrush main body 1001 and a replacement brush 50. Electric toothbrush main body 1001 includes a case 1010 forming toothbrush handle portion 102, a motor 20, an eccentric rod 30, and a stem 40 having such a form as to extend along a center axis 30t. Case 10 is formed in a tube shape. Case 10 is grasped by a user of electric toothbrush 100. Case 10 has a surface on which a control part 13 such as control panel 300 may be provided.

Motor 20 is incorporated near a first end 1011 of case 1010. Motor 20 has a driving shaft 21. Motor 20 is connected to a predetermined power supply (not shown) incorporated in case 1010, in order to rotate driving shaft 21. Eccentric rod 30 is formed in an almost bar shape. Eccentric rod 30 has a weight part 33b. Weight part 33b has a barycenter position which is displaced outward from center axis 30t of eccentric rod 30 (downward in FIG. 9). In other words, weight part 33b is eccentric with respect to center axis 30t of eccentric rod 30. Eccentric rod 30 has a second end 32 side connected to driving shaft 21.

Stem 40 has a cylinder shape (a cap shape). Stem 40 has a first end 41 side which is closed, and a bearing part 44 (not shown) is provided inside the first end 41 side. Eccentric rod 30 has a first end 31 which is inserted into bearing part 44. Stem 40 is attached to the case 1010 side so as to cover eccentric rod 30. Cylinder-shaped leading end part 41 of stem 40 is smaller in diameter than the other region of stem 40. Replacement brush 50 has a tubular part 51 which has an open trailing end 51b, a holding part 51a which is formed inside a leading end side of tubular part 51 and holds leading end part 41 of stem 40, and a brush part 52 which is provided outside the leading end side of tubular part 51. Tubular part 51 of replacement brush 50 is attached outside stem 40 so as to cover stem 40.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A powered toothbrush apparatus with capacitive touch control, the toothbrush apparatus comprising:
   a motor;
   a handle portion;
   a capacitive touch control panel in the handle portion;
   a plurality of capacitance sensors operably associated with the control panel, each of the plurality of capacitance sensors having a capacitance value that is changed by a user pressing a specific location of the control panel, thereby activating the capacitance sensor; and
   a microprocessor in the handle portion, the microprocessor electrically connected to the plurality of capacitance sensors and the motor, the microprocessor configured to: (1) detect changes in the capacitance values of the plurality of capacitance sensors; and (2) change an operating mode of the toothbrush apparatus based on the changes in capacitance values;
   wherein each sensor of the plurality of capacitance sensors is arranged in a pair with a corresponding conductive sensor target separated from the sensor by a distance and supported by a deformable actuation portion of the control panel which is deformable by the application of finger pressure by the user, wherein changing the distance between the sensor and the sensor target by applying finger pressure to the deformable portion changes the capacitance associated with the sensor and sensor target pair; and
   further comprising a spacer disposed between adjacent sensors, the spacer maintaining the distance between each paired sensor and sensor target and formed of a rigid material which is not deformable by application of finger pressure.

2. The toothbrush apparatus of claim 1, wherein the operating mode changed is motor speed.

3. The toothbrush apparatus of claim 1, wherein the operating mode changed is an on or off state of the motor.

4. The toothbrush apparatus of claim 1, wherein the user pressing a first specific location on the elastically deformable portion of the control panel turns the toothbrush apparatus on or off.

5. The toothbrush apparatus of claim 1, wherein touching a second specific location on the elastically deformable portion of the control panel changes speed of the motor.

6. The toothbrush apparatus of claim 1, wherein the sensor targets are formed by a sheet or film of conductive metal applied to the underside of the deformable portion of the control panel.

7. The toothbrush apparatus of claim 1, wherein the sensors are mounted on a printed circuit board in axially spaced apart relationship, the circuit board located below the control panel.

8. A powered toothbrush apparatus with capacitive touch control, the toothbrush comprising:
   a motor;
   a handle portion;
   a capacitive touch control panel mounted in the handle portion, the control panel being elastically deformable in response to the application of inward directed finger pressure by a user;
   a plurality of capacitance sensor buttons mounted in the handle portion, each capacitance sensor button including a capacitance sensor and a corresponding movable conductive sensor target disposed on the control panel above the sensor, the sensor target being movable towards its corresponding sensor in response to a user applying finger pressure to the control panel adjacent the sensor target which changes a capacitance of the sensor button;
   a microprocessor mounted in the handle portion and electrically connected to the sensors and the motor, the microprocessor being configured to:
   detect changes in the capacitance values of the plurality of capacitance sensor buttons; and
   change speed of the motor based on detecting changes in the capacitance values of the plurality of capacitance sensor buttons.

* * * * *